(12) United States Patent
Sandhu

(10) Patent No.: US 9,102,933 B1
(45) Date of Patent: Aug. 11, 2015

(54) TARGETED PECTIN HYDROLYSIS BY RECOMBINANT E. COLI EXPRESSING CHIMERIC PECTINASES TO FACILITATE COFFEE FERMENTATION

(76) Inventor: Charanjit Sandhu, Mississauga (CA)

( * ) Notice: Subject to any disclaimer, the term of this patent is extended or adjusted under 35 U.S.C. 154(b) by 1135 days.

(21) Appl. No.: 12/382,249

(22) Filed: Mar. 11, 2009

Related U.S. Application Data

(60) Provisional application No. 61/035,529, filed on Mar. 11, 2008.

(51) Int. Cl.
| | |
|---|---|
| C12N 1/20 | (2006.01) |
| C12N 15/00 | (2006.01) |
| C07H 21/04 | (2006.01) |
| C12N 9/18 | (2006.01) |
| C12N 9/26 | (2006.01) |
| C12N 15/09 | (2006.01) |
| C12N 9/24 | (2006.01) |
| A23F 5/02 | (2006.01) |

(52) U.S. Cl.
CPC . *C12N 15/09* (2013.01); *A23F 5/02* (2013.01); *C12N 9/18* (2013.01); *C12N 9/2402* (2013.01)

(58) Field of Classification Search
CPC ........ C12N 15/09; C12N 9/18; C12N 9/2402; A23F 5/02
See application file for complete search history.

(56) References Cited

PUBLICATIONS

Hoondal et al. Appl Microbiol Biotechnol (2002) 59:409-418.*
Stewart et al. Biotechnology and Genetic Engineering Reviews, 14:67-143, 1997.*
BRENDA Database—EC 3.2.1.15—polygalacturonase, retrieved from the internet via http://www.brenda-enzymes.info/php/result_flat.php4?ecno=3.2.1.15 on Jun. 15, 2011.*
Sugamata et al. Applied and Environmental Microbiology, Feb. 2005, 656-662.*
Coffee Review. Coffee Reference Section. 2001. Revtrieved from the internet via www.coffeereview.com.*
Current Protocols in Protein Science. John Wiley & Sons, Inc. (1995) 5.1-5.3.*
Ridley, et al., Pectins: structure, biosynthesis, and oligogalacturonide-related signaling. Phytochemistry., 57: 929-967, 2001.
Lang, C. and Dornenburg, H. Perspectives in the biological function and the technological application of polygalacturonases. Appl. Microbiol.Biotechnol., 53: 366-375, 2000.
Jarchau et al., Selection for transport competence of C-terminal polypeptides derived from *Escherichia coli* hemolysin: the shortest peptide capable of autonomous HlyB/HlyD-dependent secretion comprises the C-terminal 62 amino acids of HlyA. Mol.Gen.Genet., 245: 53-60, 1994.
Kenny et al., Analysis of the haemolysin transport process through the secretion from *Escherichia coli* of PCM, CAT or beta-galactosidase fused to the Hly C-terminal signal domain. Mol. Microbiol., 5: 2557-2568, 1991.
Avallone et al., Microbiological and biochemical study of coffee fermentation. Curr.Microblol., 42: 252-256, 2001.
Avallone et al., Fate of mucilage cell wall polysaccharides during coffee fermentation. J.Agric.Food Chem., 49: 5556-5559, 2001.
Blight, M.A. and Holland, I. B., Heterologous protein secretion and the versatile *Escherichia coli* haemolysin translocator. Trends Biotechnol., 12: 450-455, 1994.
Wandersman et al., TolC, an *Escherichla coli* outer membrane protein required for hemolysin secretion. Proc.Natl.Acad.Sci.U.S.A., 87: 4776-4780, 1990.
Lopez et al., Factors related to the formation of overfermented coffee beans during the wet processing method and storage of coffee. Proceedings of the 13th ASIC, Palpa, Colombia , 373-384. 1989.
Avallone et al., Involvement of pectolytic micro-organisms in coffee fermentation. International Journal of Food Science and Technology 37, 191-198. 2002.
Kester et al., Performance of selected microbial pectinases on synthetic monomethyl-esterified di- and trigalacturonates. J.Biol.Chem., 274: 37053-37059, 1999.
Garcia et al., Characterization of coffee pectin. Lebensmittel Wissenschaft und Technologie 24, 125-129. 1991.
Lim, Y.M. and Chung, M. C., Isolation and characterization of pectin methylesterase from papaya. Arch.Biochem.Biophys., 307: 15-20. 1993.
Kitamoto et al., Pectin methylesterase gene (pmeA) from *Aspergillus oryzae* KBN616: its sequence analysis and overexpression, and characterization of the gene product. Biosci.Biotechnol.Biochem., 63: 120-124, 1999.
Christhau et al., Pectin methyl esterase from *Aspergillus aculeatus*: expression cloning in yeast and characterization of the recombinant enzyme. Biochem.J., 319: 705-712, 1996.
Khanh, et al. Characterization and expression of a genomic pectin methyl esterase-encoding gene in *Aspergillus niger*. Gene., 106: 71-77, 1991.
Maldonado et al., Purification and characterization of pectinesterase produced by a strain of *Aspergillus niger*. Current Microbiology 28, 193-196. 1994.
Hugouvieux-Cotte-Pattat et al., Regulation of pectinotysis in *Erwinia chrysanthemi*, Annu.Rev.Microbiol., 50:213-57.: 213-257, 1996.
Parenicova et al., pgaA and pgaB encode two constitutively expressed endopolygalacturonases of *Aspergillus niger*. Biochem.J., 345 Pt 3:637-44.: 637-644, 2000.
Gadenerg, O.V. and Orskov, I., In vitro cytotoxic effect of alpha-hemolytic *Escherichia coli* on human blood granulocytes. Infect. Immun., 45: 255-260, 1984.

(Continued)

*Primary Examiner* — Yong Pak

(57) ABSTRACT

A method for fermenting coffee beans is disclosed. Bacteria secreting chimeric proteins comprising endo polygalacturane A (PGAA) and pectin methyl esterase 1 (PME1), which target the pectin coating for hydrolysis, are described. The net result of this targeted hydrolysis of the inner pectin coating can be the production of coffee beans with unique and unexpected flavor characteristics. Desirable flavors can be created or enhanced without any of the adverse taste qualities associated with artificial flavors. For lower grade coffee beans, this process serves to reduce or eliminate undesirable flavors.

20 Claims, 2 Drawing Sheets

(56) References Cited

PUBLICATIONS

Stanley et al., Fatty acylation of two Internal lysine residues required for the toxic activity of *Escherichia coli* hemolysin. Science., 266: 1992-1996, 1994.

Gray et al., A novel C-terminal signal sequence targets *Escherichia coli* haemolysin directly to the medium. J.Cell Sci.Suppl., 11:45-57.: 45-57, 1989.

Vaughn et al, A. Observations on the microbiology of the coffee fermentation in Brazil. Food Technology 12, 57-60. 1958. (Abstract only).

Frank et al. "Bacteria Responsible for Mucilage-Layer Decomposition in Kona Coffee Cherries." Applied Microbiology. vol. 13, No. 2, Mar. 1965.

Donnet et al. "Price determinants in top-quality e-auctioned specialty coffees." Agricultural Economics, 38, pp. 267-276 (2008).

Feria-Morales. "Examining the case of green coffee to illustrate the limitations of grading systems/expert tasters in sensory evaluation for quality control." Food Quality and Preference, 13, pp. 355-367 (2002).

Baldwin et al. "Electronic Noses and Tongues: Applications for the Food and Pharmaceutical Industries." Sensors, 11, pp. 4744-4766 (2011).

Donnet et al. "Effect of Sensory and Reputation Quality Attributes on Specialty Coffee Prices." American Agricultural Economics Association Annual Meeting, Long Beach, California, Jul. 23-26, 2009.

Lingle. "The Coffee Cupper's Handbook Systematic Guide the Sensory Evaluation of Coffee's Flavor." Fourth Ed. Specialty Coffee Association of America, Long Beach, California (2011).

Bertrand et al., Climatic factors directly impact the volatile organic compound fingerprint in green *arabica* coffee bean as well as coffee beverage quality, Food Chemistry, vol. 135, pp. 2575-2583, 2012.

Evangelista et al., Inoculation of starter cultures in a semi-dry coffee (Coffee *arabica*) fermentation process, Food Microbiology, 44, pp. 87-95, 2014.

Masoud et al., Yeast involved in fermentation of *Coffea arabica* in East Africa determined by genotyping and by direct denaturating gradient gel electrophoresis, Yeast, vol. 21, pp. 549-556, 2004.

Masoud et al., Pectin degrading enzymes in yeasts involved in fermentation of *Coffea arabica* in East Africa, International Journal of Food Microbiology, vol. 110, pp. 291-296, 2006.

Masoud et al., The effects of yeasts involved in the fermentation of *Coffea arabica* in East Africa on growth and ochratoxin A (OTA) production by *Aspergillus ochraceus*, International Journal of Food Microbiology, vol. 106, pp. 229-234, 2006.

Masoud et al., Influence of volatile compounds produced by yeasts predominant during processing of *Coffea arabica* in East Africa on growth and ochratoxin A (OTA) production by *Aspergillus ochraceus*, Yeast, vol. 22, pp. 1133-1142, 2005.

Silva et al., Evaluation of a potential starter culture for enhance quality of coffee fermentation, World Journal of Microbiology and Biotechnology, vol. 29, pp. 235-247, 2013.

\* cited by examiner

Figure 1. Sequence of each of 4 proteins.

SEQ ID NO: 1
1. Pectin Methyl Esterase 1(PME1) – Hemolysin A (HlyA) Chimeric Protein. PME1 amino acid sequence is shown in black. C-terminal 116 amino acids of HlyA used to form the chimeric protein are shown in red. Amino acids listed in blue were added to form an appropriate restriction site between the two regions.

MVKSVLASALFAVSALAASRTTAPSGAIVVAKSGGDYTTIGDA
IDALSTSTTDTQTIFIEEGTYDEQVYLPAMTGKVIIYGQTENTD
SYADNLVTITHAISYEDAGESDDLTATFRNKAVGSQVYNLNIA
NTCGQACHQALALSAWADQQGYYGCNFTGYQDTLLAQTGNQ
LYINSYIEGAVDFIFGQHARAWFQNVDIRVVEGPTSASITANGR
SSETDTSYYVINKSTVAAKEGDDVAEGTYYLGRPWSEYARVV
FQQTSMTNVINSLGWTEWSTSTPNTEYVTFGEYANTGAGSEGT
RASFAEKLDAKLTITDILGSDYTSWVDTSYFVDITFRNWFEKES
GDISNHEIEQIFDKSGRIITPDSLKKALEYQQRNNKASYVYGND
ALAYGSQGDLNPLINEISKIISAAGSFDVKEERTAASLLQLSGN
ASDFSYGRNSITLTTSA

SEQ ID NO: 2
2. Endo-polygalacturonase A (pgaA) – Hemolysin A Chimeric Protein. PgaA amino acid is shown in black. C-terminal 116 amino acids of HlyA used to form the chimeric protein are shown in red. Amino acids listed in blue were added to form an appropriate restriction site between the two regions.

HMPSAKPLFCLATLAGAALAAPAPSRVSDFTKRSTCTFTDAAT
ASESKTSCSDIVLKDITVPAGETLNLKDLNDGTTVTFEGTTTW
EYEEWDGPLLRISGKDITVTQSSDAVLDGNGAKWWDGEGTNG
GKTKPKFFYAHDLDDSKISGLYIKNTPVQAISVESDNLVIEDVT
IDNSDGDSEGGHNTDGFDISESTYITITGATVKNQDDCVAINSG
ENIYFSGGTCSGGHGLSIGSVGGRDDNTVKNVTFIDSTVSDSEN
GVRIKTVYDATGTVEDITYSNIQLSGISDYGIVIEQDYENGDPT
GTPSNGVTISDVTLEDITGSVDSDAVEIYILCGDGSCSDWTMSG
IDITGGETSSDCENVPSGASCDQGTITFRNWFEKESGDISNHEI
EQIFDKSGRIITPDSLKKALEYQQRNNKASYVYGNDALAYGSQ
GDLNPLINEISKIISAAGSFDVKEERTAASLLQLSGNASDFSYG
RNSITLTTSA

SEQ ID NO: 3
3. Hemolysin B (hlyB) amino acid sequence.

MDSCHKIDYGLYALEILAQYHNVSVNPEEIKHRFDTDGTGLGL
TSWLLAAKSLELKVKQVKKTIDRLNFISLPALVWREDGCHFIL

TKVSKEANRYLIFDLEQRNPRVLEQSEFEALYQGHIILIASRSS
VTGKLAKFDFTWFIPAIIKYRKIFIETLVVSVFLQLFALITPLFF
QVVMDKVLVHRGFSTLNVITVALSVVVVFEIILSGLRTYIFAHS
TSRIDVELGAKLFRHLLALPISYFESRRVGDTVARVRELDQIRN
FLTGQALTSVLDLLFSIFFAVMWYYSPKLTLVILFSLPCYAAW
SVFISPILRRRLDDKFSRNADNQSFLVESVTAINTIKAMAVSPQ
MTNIWDKQLAGYVAAGFKVTVLATIGQQGIQLIQKTVMIINLW
LGAHLVISGDLSIGQLIAFNMLAGQIVAPVIRLAQIWQDFQQV
GISVTRLGDVLNSPTESYHGKLALPEINGDITFRNIRFRYKPDS
PVILDNINLSIKQGEVIGIVGRSGSGKSTLTKLIQRFYIPENGQV
LIDGHDLALADPNWLRRQVGVVLQDNVLLNRSIIDNISLANPG
MSVEKVIYAAKLAGAHDFISELREGYNTIVGEQGAGLSGGQRQ
RIAIARALVNNPKILIFDEATSALDYESEHVIMRNMHKICKGRT
VIIAHRLSTVKNADRIIVMEKGKIVEQGKHKELLSEPESLYSY
LYQLQSD

SEQ ID NO: 4
4. Hemolysin D (HlyD) amino acid sequence.

HMKTWLMGFSEFLLRYKLVWSETWKIRKQLDTPVREKDENEF
LPAHLELIETPVSRRPRLVAYFIMGFLVIAFILSVLGQVEIVATA
NGKLTLSGRSKEIKPIENSIVKEIIVKEGESVRKGDVLLKLTAL
GAEADTLKTQSSLLQARLEQIRYQILSRSIELNKLPELKLPDEP
YFQNVSEEEVLRLTSLIKEQFSTWQNQKYQKELNLDKKRAERL
TILARINRYENVSRVEKSRLDDFRSLLHKQAIAKHAVLEQENK
YVEAANELRVYKSQLEQIESEILSAKEEYQLVTQLFKNEILDKL
RQTTDSIELLTLELEKNEERQQASVIRAPVSGKVQQLKVHTEG
GVVTTAETLMVIVPEDDTLEVTALVQNKDIGFINVGQNAIIKV
EAFPYTRYGYLVGKVKNINLDAIEDQKLGLVFNVIVSVEENDL
STGNKHIPLSSGMAVTAEIKTGMRSVISYLLSPLEESVTESLHE
R

TARGETED PECTIN HYDROLYSIS BY RECOMBINANT *E. COLI* EXPRESSING CHIMERIC PECTINASES TO FACILITATE COFFEE FERMENTATION

RELATED APPLICATIONS

The present application claims the benefit of U.S. Provisional Patent Application No. 61/035,529, filed Mar. 11, 2008, the contents of which are incorporated herein by reference.

SEQUENCE LISTING

This application incorporates-by-reference the material included on a written copy of a sequence listing included with the application, as well as on a computer readable copy of the sequence listing submitted on one compact disc. The disc was created on Jul. 30, 2009, and includes one 20 KB file entitled, "SQL34766 2003 ST25.txt." The copy of the computer readable form of the sequence listing is identical to the written copy of the sequence listing, and thus, the computer readable copy includes no new matter.

FIELD

The invention relates to the use of pectinases for coffee fermentation.

BACKGROUND OF THE INVENTION

The preparation of coffee beans for consumption is a tightly choreographed process. Coffee cherries are harvested upon ripening and then both mechanical and biological processes are employed to recover a coffee bean from each cherry. The production process begins by the mechanical removal of both the outer covering (exocarp) and the pulp (outer mesocarp) in a process referred to as depulping.

A poorly understood fermentation step that has long been speculated to result in hydrolysis of the inner pectin coating is important for the production of suitable coffee beans. Briefly, this step involves soaking coffee beans in a vat of untreated water for approximately 15 to 20 hours. The completion of the fermentation step is then signaled by coffee beans undergoing textural changes to their pectin coating, which is thought to represent the hydrolysis of this layer. Frequent over fermentation results in spoilage and loss of product. Upon the completion of fermentation, the coffee beans are then washed, dried and are ready for roasting to produce the final product.

The fermentation process has been speculated to target the pectin coating of coffee beans. Pectin itself consists of linear polymers of alpha 1-4 linked D-galacturonic acid[1]. The carboxyl groups are frequently methylated to yield the corresponding ester. The degree of esterification (DE) refers to the ratio of esterified galactouronic groups to the total number of groups, and is used to classify pectin as either high methoxyl pectin (HM) or low methoxyl pectin (LM) at 50% DE'. The functional significance of the DE is its relationship to pectin solubility, gel forming abilities and availability for hydrolysis. Pectins with a lower degree of esterification can enter solution at a lower temperature and require a lower pH for precipitation due to their relative greater hydrophobicity of ester groups when compared with carboxy groups[1].

The hydrolysis of pectin is mediated by four classes of enzymes: pectin methyl esterase (PME), polygalactouronases (PG), pectin lyase (PL) and rhamnogalacturonases (RHG)[2]. The activity of polygalacturonases may be further classified as having either endo- or exo-polygalacturonase activity. Endo-polygalacturonases catalyze the hydrolysis of 1,4-alpha-D-galacturosiduronic linkages between two non-methylated galacturonic acid residues while exo-polygalacturonases remove terminal residues. While, pectin methyl esterases (PME) function to reduce the esterification of pectin and as a consequence create a substrate that is then available for hydrolysis by polygalacturonases[2].

The inner pectin coating has been hypothesized to be degraded by both bacterial and endogenous coffee bean enzymes[3,4]. The development of an acidic environment (pH 5.3-3.5) during the course of fermentation was thought to reflect the growth of presumed pectinolytic bacteria[5]. Changes in the texture and feel of the pectin coating after fermentation have been presumed to represent the hydrolysis of the pectin coating and signals to coffee producers the point at which fermentation should be terminated[6]. An incomplete removal of the inner mesocarp has been postulated to act as substrate for subsequent bacterial fermentation and spoilage of the bean[7].

Frequent under- or over-fermentation will result in taste defects in the end product and may require disposal of the product[8]. Yeast overgrowth from a prolonged fermentation, due to their greater tolerance of an acidic environment is thought to be responsible for the taste defects that arise from over-fermentation. Specifically, ethanol production in addition to other organic acids from yeast is thought to be the principal mediator of the bitter taste associated with over-fermentation[9].

More recent studies have suggested that the role of bacterial enzymes in fermentation may be dramatically limited in terms of their significance[6]. An examination of the fermentation microflora revealed that the proportion of pectinolytic bacteria remained relatively stable during fermentation[5]. Instead, non-pectinolytic lactic acid bacteria and yeast comprised the majority of cell growth, again presumably due to their greater tolerance of acidic conditions[5]. Pectinolytic bacteria that were recovered from the fermentation process included only those with limited pectinolytic activity, *Erwinia herbicola* and *Klebsiella pneumoniae*[5]. An innoculum enriched with these organisms failed to accelerate or alter fermentation in any meaningful manner to further refute earlier theories of their significance in coffee bean fermentation[10]. Yeast capable of pectinolysis have yet to be recovered from a fermentation reaction[11].

The pectin coating that covers coffee beans exists in a highly esterified form[12]. As a consequence of this degree of esterification, the activity of pectin methyl esterases are essential to deesterify the pectin which then allows for subsequent substrate availability and hydrolysis by polygalacturonases. It has been observed that without deesterification the pectin would remain essentially unhydrolyzable by bacterial polygalacturonases[2]. Bacteria recovered from coffee fermentation reactions have to date been repeatedly shown to lack the activity to depolymerize esterified pectins[10]. The in vitro pectylase activity that has been recovered from bacteria present in coffee fermentation reactions was relatively inactive at the low pH environment at which the fermentation reaction occurs. Instead in vitro assays showed that the maximum catalytic activity for these enzymes was within the alkaline pH range[10]. Bacteria with polygalacturonase activity compatible with the acidic conditions of fermentation were present in relatively low levels although as previously mentioned they were unable to hydrolyze highly methylated pectin[5]. Hence, the current view is that bacterially expressed pectinases have no significant role in coffee fermentation.

This notion is further reinforced by examination of coffee beans post fermentation to reveal that only modest depolymerization and limited hydrolysis of the pectin covering occurs[6].

In summary, the limited growth of pectinolytic bacteria during the fermentation process, an absence of PME activity and finally the basic pH requirements of the limited pectinolytic activity that was present are all strongly suggestive of the current view that bacteria play a very limited or no role in directly mediating pectin hydrolysis. Avallone et al. have proposed an alternative mechanism that bacterially produced organic acids (lactic and acetic acid) decrease the environmental pH to induce conformational changes in pectin that results in it subsequent depolymerization[6]. This current view of coffee fermentation is in sharp contrast to previous theories that bacterial enzymes drive fermentation by catalyzing pectin hydrolysis.

BRIEF DESCRIPTION OF THE FIGURES

FIG. 1 shows the sequences of chimeric proteins comprising pectin methyl esterase (PME1)-Hemolysin A (HlyA): SEQ ID NO: 1, endo-polygalacturonase A (pgaA)-HlyA: SEQ ID NO: 2, hemolysin B (hly B): SEQ ID NO: 3, hemolysin D (hly D): SEQ ID NO: 4.

DESCRIPTION OF THE INVENTION

An embodiment of this invention relates to bacteria secreting chimeric proteins comprising endo polygalacturane A (PGAA) and pectin methyl esterase 1 (PME1), which target the pectin coating for hydrolysis. The net result of this targeted hydrolysis of the inner pectin coating can be the production of coffee beans with unique and unexpected flavour characteristics. Specifically, fruitiness can be enhanced and a new taste note of chocolateness can be created without any of the adverse taste qualities associated with artificial flavours. For lower grade coffee beans, this process serves to reduce or eliminate undesirable flavours such as woody, tobacco, earthy and fermented.

Overview of Recombinant Bacteria

According to an embodiment of this invention, recombinant bacteria have been created that can target the pectin coating present on coffee beans for hydrolysis. The presence of esterified pectin on the surface of the bean can require that a pectin methyl esterase is employed that is able to function under the low pH environment at which coffee fermentation occurs. Once the pectin is demethylated, a second enzyme, a polygalacturonase, can be required to hydrolyze the pectin. Finally, as most recombinant bacterial proteins remain localized within the cell, chimeric forms of these proteins can be required to export these proteins into the extracellular environment Pectin Methylesterase Pectin methylesterase (PME) catalyzes the hydrolysis of methyl ester groups linked to galacturonic acid residues that comprise pectin. Partial to complete hydrolysis of these ester groups is a prerequisite for the further hydrolysis of pectin. Qualitatively, enough esters should be hydrolyzed to produce a substantial change in the taste of the coffee. PME has been found in both fruits of several higher plants, bacteria and in filamentous fungi. The PME from higher plants and bacteria typically have optimal activity at a pH range between 7 and 8[13], whereas fungal PMEs typically operate best at a pH range of 3 to 4[14,15]. Consequently, fungal PMEs may be better suited to the acidic conditions of fermentation.

A total of three fungal PMEs have been reported to date from various *Aspergillus* species[14-16]. The PME cloned from *Aspergillus oryzae* (PMEA) was found to have maximum activity at a pH of 5.0 and temperature of 55° C.[14]. As the fermentation process would typically not reach this temperature, this isoform of PME may not be well suited to catalyze deesterification during coffee fermentation under typical conditions. The PME cloned from *Aspergillus Niger* has been reported to have a Tmax of 45° C. (10 to 15 degrees less than *A. Oryzae*) and an optimal pH of 5.0[17]. It is noted that, under typical conditions, PME from *A. niger* experiences competitive and non-competitive inhibition from the products of hydrolysis: polygalaturonic acid and methanol[17]. Finally, the third PME homolog, which can be recovered from *Aspergillus Aculeatus*[15], is the most preferred. The PME recovered from this organism can be ideal for catalysis of coffee fermentation for several reasons[15]. To begin with, maximum activity occurs at a pH of 4.6 and temperature of 45° C., where 90 percent of the activity is present between 35 to 50 degrees Celsius. Furthermore, the activity of PME recovered from *A. Aculeatus* was not subject to feedback inhibition from high concentrations of methanol or the presence of polygalacturonic acid (the products of the reaction)[15]. This is in contrast to PME from *A. Niger* which was sensitive to feedback inhibition[17].

In summary, *A. Aculeatus* PME1 (Gen Bank Accession Number: 449378) is preferred for deesterification of the coffee bean pectin, under typical conditions, due to its physical functional range and the absence of product feedback inhibition. This protein can be fused at the C-terminus to the hemolysin (HlyA) signal sequence to produce polypeptide SEQ ID NO: 1 to facilitate secretion from recombinant bacteria.

Polygalacturonase

Polygalacturonase catalyzes the hydrolysis of pectin and most isoforms of it hydrolyze deesterified pectin with a much greater efficiency. Plants, fungi and bacteria have all been found to express various PG isoforms, which may be divided into those with endo (can cleave internally) or exo (hydrolyzed the reaction from the ends) activity. Studies of bacterial PG have focused predominantly on PehX, the *Erwinia* PG[18]. The low pH at which coffee fermentation occurs would not be well suited to the higher pH requirements of PehX for maximum enzyme activity[18].

The source of most commercial sources of PG arises from *Aspergillus Niger*. Here, seven different PG isoforms exist with different pectin specificites[11]. Furthermore, this family of enzymes has been shown to have maximum activity under acidic conditions. PG isoforms capable of hydrolyzing pectin with a high degree of esterification included pgaA (PGA) and pgaB (PGB)[11]. PGB has been shown to have greater activity on methylated pectin, although PGA peak activity occurs at a lower pH (pH=4)[19]. Ideally, a PG with the pH requirements of PGA and the ability of PGB to hydrolyze highly esterified pectin can be ideal for coffee fermentation. According to an embodiment of this invention, a recombinant bacterial strain expressing both PME and PGA is presented.

Protein Export

Recombinant proteins expressed by bacteria typically localize within the cytoplasm or periplasm. Specific signal sequences are required for the export of proteins into the extracellular environment. The hemolysin transporter system can be utilized to export PME and PGA into the extracellular environment. Hemolysin A, a component of the hemolysin transporter system mediates its toxic effect by inducing hemolysis upon its insertion into the plasma membrane of red blood cells[20]. Acetylation of hlyA by hlyC is required for its toxic activation[21]. According to an embodiment of the present invention, the hlyC gene is not introduced into the transgenic bacteria and only the C-terminal domain of hlyA, which contains none of the hemolytic properties associated with hemolysin A, can be used. Together, this helps to ensure the partial or complete absence of any pathogenic properties in the resulting recombinant bacteria.

Export mediated by hemolysin proteins requires the C-terminal 50 amino acids of HlyA fused to the target protein[22-24], in addition, 2 translocator proteins HlyB (GenBank Accession Number: M81823), HlyD[25] and an endogenous outer membrane protein, TolC[26] form a trimeric exit pore for release of the hybrid protein. According to an embodiment of the present invention, chimeric forms of PME and PGA can be created by fusing the C-terminal of HlyA to the C-termini of the respective proteins to be target for export. Other molecular export systems as are known in the art can be suitable to export the chimeric proteins. In addition, HlyB and HlyD can be coexpressed to ensure formation of a pore for transport of the pectinases into the extracellular environment.

According to an embodiment of the invention, the DNA encoding the chimeric proteins can comprise a restriction site. The restriction site can be situated between the pectinase and the HlyA sequence and can be useful to allow changes to the DNA construct.

Examples

Materials and Methods

Vector Production

Synthetic gene constructs were purchased of each of the following genes: PME1, PGA, HlyB and HlyD from the GenScript Corporation. The C-terminal 50 amino acid coding sequence of HlyA was fused to the C-terminal of PME1 and PGA to create chimeric forms of these proteins. FIG. 1 provides the amino acid sequence of each protein. The cDNAs were then cloned into the Novagen PetDUET vector which allows for the expression of two recombinant proteins from each vector. The following plasmids were constructed: 1) PME1+PGA and 2) HlyB+HlyD. *E. coli* strain DH5α was then transformed with both vectors by the GenScript Corporation using methods known in the art.

Fermentation

Ripe coffee cherries were manually depulped prior to fermentation to recover strictly hard bean (shb) Costa Rican coffee beans. Bacteria were grown in Luria-Bertani broth (LB) containing 30 µg/ml kanamycin and 50 µg/ml ampicillin to an optical density ($OD_{595}$) of 1.0. Bacterial cells were then induced with 4 mM isopropyl-beta-D-thiogalactopyranoside (IPTG) at 32° C. for 30 minutes. Coffee beans were then added to the inoculum and the reaction incubated for 16 hours at 32° C. Coffee beans were then washed and dried for 2 weeks at room temperature prior to roasting. Coffee beans were roasted only when moisture levels for each bean were less than 10%.

Tasting

Coffee was tasted and scored on a scale of 1-10 for a total of 23 taste sensations: acidity, body, fruity, winey, nutty, chocolatey, floral, smooth, sweet, salty, herbal, woody, astringent, tobacco, musty, earthy, rubbery, phenolic, fermented, chemical, metallic, past crop and baggy. For each trial of tasting, a standard, control (Costa Rican Standard) and experimental sample were prepared in triplicate. This was performed for both intermediate and low-grade coffee beans. Each sample was tasted by 2 independent tasters that were blinded.

Results

The fermentation of coffee beans with recombinant bacteria conferred unique and unexpected taste properties to the end product. Table 1 summarizes the results after treatment of intermediate grade coffee beans. Coffee flavours were scored on a scale of 1 to 10 for each flavour note. Novel flavours were introduced and some desirable flavours were enhanced. New flavours introduced included both chocolate and nutty flavours. Furthermore, the chocolate note was absent of the alcohol note that is characteristically present in artificially flavoured coffees. Flavour notes that were improved included both sweetness and smoothness. For lower grade coffee beans, undesirable flavours were reduced or eliminated. These included woody, tobacco, earthy and fermented flavours. Table 2 summarized these tasting results on a scale of 1 to 10 for each flavour note

TABLE 1

Mean taste scores from control and recombinant bacterial fermentation of intermediate-grade coffee

| Taste Attribute | Control | Enzyme |
| --- | --- | --- |
| Acidity | 6 | 6 |
| Body | 5 | 5 |
| Fruity | 2 | 4 |
| Winey | 0 | 0 |
| Nutty | 0 | 3 |
| Chocolatey | 0 | 8 |
| Floral | 0 | 1 |
| Smooth | 2 | 6 |
| Sweet | 0 | 4 |
| Salty | 0 | 0 |
| Herbal | 0 | 0 |
| Woody | 0 | 0 |
| Astringent | 0 | 0 |
| Tobacco | 0 | 0 |
| Musty | 0 | 0 |
| Earthy | 0 | 0 |
| Rubberry | 0 | 0 |
| Phenolic | 0 | 0 |
| Fermented | 0 | 0 |
| Chemical | 0 | 0 |
| Metallic | 0 | 0 |
| Past Crop | 0 | 0 |
| Baggy | 0 | 0 |

Coffee production is a multistep process of which a critical step is the fermentation of coffee beans. Current evidence suggests that this step results in only modest depolymerization secondary to acidic changes that occur in the environment and limited hydrolysis of pectin from pectinase activity most likely present within the ripe coffee cherry. The present invention is directed to a novel approach to this process. The process comprises bacteria that secrete chimeric proteins for the purpose of hydrolyzing the pectin coating present on coffee beans. The net result of this novel process is the creation of coffee with unique flavour characteristics. Specifically, a novel chocolate note is present that is absent of the alcohol note that characterizes artificially flavoured coffee. In addition, undesirable flavours of woody, tobacco, earthy and fermented were substantially reduced or eliminated. This novel process results in a superior tasting alternative to existing flavoured or unflavoured coffees.

TABLE 2

Mean taste scores from control and recombinant bacterial fermentation of low-grade coffee beans.

| Taste Attribute | Control | Enzyme |
|---|---|---|
| Acidity | 3.8 | 5.8 |
| Body | 6.8 | 5.9 |
| Flavour | 1.0 | 5.8 |
| Woody | 8.0 | 0.4 |
| Tobacco | 4.5 | 0 |
| Earthy | 7.5 | 0 |
| Fermented | 7.0 | 0.1 |

As will be understood by those of ordinary skill in the relevant arts, once they have been made familiar with this disclosure, a variety of different methods can be suitable for use in implementing the present invention. While the invention has been described and illustrated in connection with various embodiments, many variations and modifications, as will be evident to those skilled in the relevant arts, can be made without departing from the spirit and scope of the invention, and the invention is thus not to be limited to the precise details of methodology or construction set forth above as such variations and modifications are intended to be included within the scope of the invention. Except to the extent necessary or inherent in the processes themselves, no particular order to steps or stages of methods or processes described in this disclosure, including the Figures, is implied. In many cases the order of process steps can be varied without changing the purpose, effect, or import of the methods described.

It will be appreciated by those skilled in the relevant arts, from a reading of the disclosure, that various changes in form and detail can be made without departing from the true scope of the invention in the appended claims.

All of the references cited herein are hereby incorporated by reference in their entirety.

What is claimed is:

1. A method for fermenting coffee beans through the use of microorganisms, said method comprising the steps of:
    combining depulped coffee beans with microorganisms transformed with one or more chimeric proteins comprising pectinases to produce a mixture;
    incubating the mixture for a period of time; and
    isolating the incubated coffee beans;
    wherein the activity of the pectinases during the fermentation process alters the flavor of coffee produced from the isolated coffee beans to be free from undesirable flavors of woody, tobacco, earthy and fermented, and wherein the woody, tobacco, earthy and fermented flavors are assessed by taste sensation testing,
    wherein the pectinases are selected from the group comprising pectin methyl esterases and endo-polygalactouronases, and wherein the pectinases are suitable to use in an acidic environment.

2. The method according to claim 1, wherein the chimeric proteins comprise a hemolysin polypeptide.

3. The method according to claim 1, wherein the microorganisms are also transformed with hemolysin B and hemolysin D.

4. The method of claim 1, wherein the activity of the pectinases during the fermentation process alters the flavor of coffee produced from the isolated coffee beans to have a chocolate flavor, and wherein the chocolate flavor is assessed by taste sensation testing.

5. The method of claim 1, wherein the microorganisms are bacteria.

6. The method of claim 1, wherein the depulped coffee beans are combined, in any order, with water and the microorganisms transformed with one or more chimeric proteins comprising pectinases to produce the mixture.

7. The method of claim 1, wherein the activity of the pectinases during the fermentation process alters the flavor of coffee produced from the isolated coffee beans by decreasing taste scores for undesirable flavors of woody, tobacco, earthy and fermented by 2 or more units on a scale of 0 to 10 when assessed by taste sensation testing.

8. The method of claim 1, wherein the activity of the pectinases during the fermentation process alters the flavor of coffee produced from the isolated coffee beans by decreasing taste scores for undesirable flavors of woody, tobacco, earthy and fermented by 4 or more units on a scale of 0 to 10 when assessed by taste sensation testing.

9. The method of claim 1, wherein: the chimeric proteins comprise a hemolysin polypeptide; the microorganisms are also transformed with hemolysin B and hemolysin D; the depulped coffee beans are combined, in any order, with water and the microorganisms transformed with one or more chimeric proteins comprising pectinases to produce the mixture; and the activity of the pectinases during the fermentation process alters the flavor of coffee produced from the isolated coffee beans to have a chocolate flavor, and wherein the chocolate flavor is assessed by taste sensation testing.

10. The method of claim 1, wherein: the chimeric proteins comprise a hemolysin polypeptide; the microorganisms are also transformed with hemolysin B and hemolysin D; the depulped coffee beans are combined, in any order, with water and the microorganisms transformed with one or more chimeric proteins comprising pectinases to produce the mixture; the activity of the pectinases during the fermentation process alters the flavor of coffee produced from the isolated coffee beans by decreasing taste scores for undesirable flavors of woody, tobacco, earthy and fermented by 2 or more units on a scale of 0 to 10 when assessed by taste sensation testing; and the activity of the pectinases during the fermentation process alters the flavor of coffee produced from the isolated coffee beans to have a chocolate flavor, and wherein the chocolate flavor is assessed by taste sensation testing.

11. The method of claim 2, wherein the microorganisms are also transformed with hemolysin B and hemolysin D.

12. The method of claim 2, wherein the microorganisms are also transformed with hemolysin B and hemolysin D, and wherein the depulped coffee beans are combined, in any order, with water and the microorganisms transformed with one or more chimeric proteins comprising pectinases to produce the mixture.

13. The method of claim 6, wherein the activity of the pectinases during the fermentation process alters the flavor of coffee produced from the isolated coffee beans to have a chocolate flavor, and wherein the chocolate flavor is assessed by taste sensation testing.

14. The method of claim 2, wherein the microorganisms are also transformed with hemolysin B and hemolysin D, wherein the depulped coffee beans are combined, in any order, with water and the microorganisms transformed with one or more chimeric proteins comprising pectinases to produce the mixture, and wherein the activity of the pectinases during the fermentation process alters the flavor of coffee produced from the isolated coffee beans by decreasing taste scores for undesirable flavors of woody, tobacco, earthy and fermented by 2 or more units on a scale of 0 to 10 when assessed by taste sensation testing.

15. The method of claim 2, wherein the microorganisms are also transformed with hemolysin B and hemolysin D, wherein the depulped coffee beans are combined, in any order, with water and the microorganisms transformed with one or more chimeric proteins comprising pectinases to produce the mixture, and wherein the activity of the pectinases during the fermentation process alters the flavor of coffee produced from the isolated coffee beans by decreasing taste scores for undesirable flavors of woody, tobacco, earthy and fermented by 4 or more units on a scale of 0 to 10 when assessed by taste sensation testing.

16. The method of claim 15, wherein the activity of the pectinases during the fermentation process alters the flavor of coffee produced from the isolated coffee beans to have a chocolate flavor, and wherein the chocolate flavor is assessed by taste sensation testing.

17. The method of claim 1, wherein the pectin methyl esterase comprises an amino acid sequence as shown in SEQ ID NO: 1 and the endo-polygalactouronase comprises an amino acid sequence as shown in SEQ ID NO: 2.

18. The method of claim 1, wherein the chimeric proteins comprise the amino acid sequence of SEQ ID NO: 1 and the amino acid sequence of SEQ ID NO: 2.

19. The method of claim 6, wherein the chimeric proteins comprise the amino acid sequence of SEQ ID NO: 1 and the amino acid sequence of SEQ ID NO: 2.

20. The method of claim 13, wherein the chimeric proteins comprise the amino acid sequence of SEQ ID NO: 1 and the amino acid sequence of SEQ ID NO: 2.

* * * * *

SEQUENCE LISTING

<160> NUMBER OF SEQ ID NOS: 4

<210> SEQ ID NO 1
<211> LENGTH: 449
<212> TYPE: PRT
<213> ORGANISM: A. Aculeatus

<400> SEQUENCE: 1

```
Met Val Lys Ser Val Leu Ala Ser Ala Leu Phe Ala Val Ser Ala Leu
1               5                   10                  15

Ala Ala Ser Arg Thr Thr Ala Pro Ser Gly Ala Ile Val Val Ala Lys
                20                  25                  30

Ser Gly Gly Asp Tyr Thr Thr Ile Gly Asp Ala Ile Asp Ala Leu Ser
            35                  40                  45

Thr Ser Thr Thr Asp Thr Gln Thr Ile Phe Ile Glu Glu Gly Thr Tyr
    50                  55                  60

Asp Glu Gln Val Tyr Leu Pro Ala Met Thr Gly Lys Val Ile Ile Tyr
65                  70                  75                  80

Gly Gln Thr Glu Asn Thr Asp Ser Tyr Ala Asp Asn Leu Val Thr Ile
                85                  90                  95

Thr His Ala Ile Ser Tyr Glu Asp Ala Gly Glu Ser Asp Asp Leu Thr
            100                 105                 110

Ala Thr Phe Arg Asn Lys Ala Val Gly Ser Gln Val Tyr Asn Leu Asn
        115                 120                 125

Ile Ala Asn Thr Cys Gly Gln Ala Cys His Gln Ala Leu Ala Leu Ser
    130                 135                 140

Ala Trp Ala Asp Gln Gln Gly Tyr Tyr Gly Cys Asn Phe Thr Gly Tyr
145                 150                 155                 160

Gln Asp Thr Leu Leu Ala Gln Thr Gly Asn Gln Leu Tyr Ile Asn Ser
                165                 170                 175

Tyr Ile Glu Gly Ala Val Asp Phe Ile Phe Gly Gln His Ala Arg Ala
            180                 185                 190

Trp Phe Gln Asn Val Asp Ile Arg Val Val Glu Gly Pro Thr Ser Ala
        195                 200                 205

Ser Ile Thr Ala Asn Gly Arg Ser Ser Glu Thr Asp Thr Ser Tyr Tyr
    210                 215                 220

Val Ile Asn Lys Ser Thr Val Ala Ala Lys Glu Gly Asp Asp Val Ala
225                 230                 235                 240
```

-continued

Glu Gly Thr Tyr Tyr Leu Gly Arg Pro Trp Ser Glu Tyr Ala Arg Val
            245                 250                 255

Val Phe Gln Gln Thr Ser Met Thr Asn Val Ile Asn Ser Leu Gly Trp
        260                 265                 270

Thr Glu Trp Ser Thr Ser Thr Pro Asn Thr Glu Tyr Val Thr Phe Gly
        275                 280                 285

Glu Tyr Ala Asn Thr Gly Ala Gly Ser Glu Gly Thr Arg Ala Ser Phe
        290                 295                 300

Ala Glu Lys Leu Asp Ala Lys Leu Thr Ile Thr Asp Ile Leu Gly Ser
305                 310                 315                 320

Asp Tyr Thr Ser Trp Val Asp Thr Ser Tyr Phe Val Asp Ile Thr Phe
                325                 330                 335

Arg Asn Trp Phe Glu Lys Glu Ser Gly Asp Ile Ser Asn His Glu Ile
            340                 345                 350

Glu Gln Ile Phe Asp Lys Ser Gly Arg Ile Ile Thr Pro Asp Ser Leu
            355                 360                 365

Lys Lys Ala Leu Glu Tyr Gln Gln Arg Asn Asn Lys Ala Ser Tyr Val
            370                 375                 380

Tyr Gly Asn Asp Ala Leu Ala Tyr Gly Ser Gln Gly Asp Leu Asn Pro
385                 390                 395                 400

Leu Ile Asn Glu Ile Ser Lys Ile Ile Ser Ala Ala Gly Ser Phe Asp
                405                 410                 415

Val Lys Glu Glu Arg Thr Ala Ala Ser Leu Leu Gln Leu Ser Gly Asn
            420                 425                 430

Ala Ser Asp Phe Ser Tyr Gly Arg Asn Ser Ile Thr Leu Thr Thr Ser
            435                 440                 445

Ala

<210> SEQ ID NO 2
<211> LENGTH: 489
<212> TYPE: PRT
<213> ORGANISM: A. Aculeatus

<400> SEQUENCE: 2

His Met Pro Ser Ala Lys Pro Leu Phe Cys Leu Ala Thr Leu Ala Gly
1               5                   10                  15

Ala Ala Leu Ala Ala Pro Ala Pro Ser Arg Val Ser Asp Phe Thr Lys
            20                  25                  30

Arg Ser Thr Cys Thr Phe Thr Asp Ala Ala Thr Ala Ser Glu Ser Lys
        35                  40                  45

Thr Ser Cys Ser Asp Ile Val Leu Lys Asp Ile Thr Val Pro Ala Gly
    50                  55                  60

Glu Thr Leu Asn Leu Lys Asp Leu Asn Asp Gly Thr Thr Val Thr Phe
65                  70                  75                  80

Glu Gly Thr Thr Thr Trp Glu Tyr Glu Glu Trp Asp Gly Pro Leu Leu
                85                  90                  95

Arg Ile Ser Gly Lys Asp Ile Thr Val Thr Gln Ser Ser Asp Ala Val
            100                 105                 110

Leu Asp Gly Asn Gly Ala Lys Trp Trp Asp Gly Glu Gly Thr Asn Gly
        115                 120                 125

Gly Lys Thr Lys Pro Lys Phe Phe Tyr Ala His Asp Leu Asp Asp Ser
    130                 135                 140

Lys Ile Ser Gly Leu Tyr Ile Lys Asn Thr Pro Val Gln Ala Ile Ser
145                 150                 155                 160

```
Val Glu Ser Asp Asn Leu Val Ile Glu Asp Val Thr Ile Asp Asn Ser
            165                 170                 175

Asp Gly Asp Ser Glu Gly Gly His Asn Thr Asp Gly Phe Asp Ile Ser
        180                 185                 190

Glu Ser Thr Tyr Ile Thr Ile Thr Gly Ala Thr Val Lys Asn Gln Asp
        195                 200                 205

Asp Cys Val Ala Ile Asn Ser Gly Glu Asn Ile Tyr Phe Ser Gly Gly
        210                 215                 220

Thr Cys Ser Gly Gly His Gly Leu Ser Ile Gly Ser Val Gly Gly Arg
225                 230                 235                 240

Asp Asp Asn Thr Val Lys Asn Val Thr Phe Ile Asp Ser Thr Val Ser
                245                 250                 255

Asp Ser Glu Asn Gly Val Arg Ile Lys Thr Val Tyr Asp Ala Thr Gly
            260                 265                 270

Thr Val Glu Asp Ile Thr Tyr Ser Asn Ile Gln Leu Ser Gly Ile Ser
        275                 280                 285

Asp Tyr Gly Ile Val Ile Glu Gln Asp Tyr Glu Asn Gly Asp Pro Thr
290                 295                 300

Gly Thr Pro Ser Asn Gly Val Thr Ile Ser Asp Val Thr Leu Glu Asp
305                 310                 315                 320

Ile Thr Gly Ser Val Asp Ser Asp Ala Val Glu Ile Tyr Ile Leu Cys
                325                 330                 335

Gly Asp Gly Ser Cys Ser Asp Trp Thr Met Ser Gly Ile Asp Ile Thr
            340                 345                 350

Gly Gly Glu Thr Ser Ser Asp Cys Glu Asn Val Pro Ser Gly Ala Ser
        355                 360                 365

Cys Asp Gln Gly Thr Ile Thr Phe Arg Asn Trp Phe Glu Lys Glu Ser
        370                 375                 380

Gly Asp Ile Ser Asn His Glu Ile Glu Gln Ile Phe Asp Lys Ser Gly
385                 390                 395                 400

Arg Ile Ile Thr Pro Asp Ser Leu Lys Lys Ala Leu Glu Tyr Gln Gln
                405                 410                 415

Arg Asn Asn Lys Ala Ser Tyr Val Tyr Gly Asn Asp Ala Leu Ala Tyr
            420                 425                 430

Gly Ser Gln Gly Asp Leu Asn Pro Leu Ile Asn Glu Ile Ser Lys Ile
        435                 440                 445

Ile Ser Ala Ala Gly Ser Phe Asp Val Lys Glu Glu Arg Thr Ala Ala
        450                 455                 460

Ser Leu Leu Gln Leu Ser Gly Asn Ala Ser Asp Phe Ser Tyr Gly Arg
465                 470                 475                 480

Asn Ser Ile Thr Leu Thr Thr Ser Ala
                485

<210> SEQ ID NO 3
<211> LENGTH: 707
<212> TYPE: PRT
<213> ORGANISM: A. Aculeatus

<400> SEQUENCE: 3

Met Asp Ser Cys His Lys Ile Asp Tyr Gly Leu Tyr Ala Leu Glu Ile
1               5                   10                  15

Leu Ala Gln Tyr His Asn Val Ser Val Asn Pro Glu Glu Ile Lys His
            20                  25                  30

Arg Phe Asp Thr Asp Gly Thr Gly Leu Gly Leu Thr Ser Trp Leu Leu
        35                  40                  45
```

-continued

```
Ala Ala Lys Ser Leu Glu Leu Lys Val Lys Gln Val Lys Lys Thr Ile
 50              55                  60
Asp Arg Leu Asn Phe Ile Ser Leu Pro Ala Leu Val Trp Arg Glu Asp
 65                  70                  75                  80
Gly Cys His Phe Ile Leu Thr Lys Val Ser Lys Glu Ala Asn Arg Tyr
                 85                  90                  95
Leu Ile Phe Asp Leu Glu Gln Arg Asn Pro Arg Val Leu Glu Gln Ser
                100                 105                 110
Glu Phe Glu Ala Leu Tyr Gln Gly His Ile Ile Leu Ile Ala Ser Arg
                115                 120                 125
Ser Ser Val Thr Gly Lys Leu Ala Lys Phe Asp Phe Thr Trp Phe Ile
130                 135                 140
Pro Ala Ile Ile Lys Tyr Arg Lys Ile Phe Ile Glu Thr Leu Val Val
145                 150                 155                 160
Ser Val Phe Leu Gln Leu Phe Ala Leu Ile Thr Pro Leu Phe Phe Gln
                165                 170                 175
Val Val Met Asp Lys Val Leu Val His Arg Gly Phe Ser Thr Leu Asn
                180                 185                 190
Val Ile Thr Val Ala Leu Ser Val Val Val Phe Glu Ile Ile Leu
                195                 200                 205
Ser Gly Leu Arg Thr Tyr Ile Phe Ala His Ser Thr Ser Arg Ile Asp
210                 215                 220
Val Glu Leu Gly Ala Lys Leu Phe Arg His Leu Leu Ala Leu Pro Ile
225                 230                 235                 240
Ser Tyr Phe Glu Ser Arg Arg Val Gly Asp Thr Val Ala Arg Val Arg
                245                 250                 255
Glu Leu Asp Gln Ile Arg Asn Phe Leu Thr Gly Gln Ala Leu Thr Ser
                260                 265                 270
Val Leu Asp Leu Leu Phe Ser Phe Ile Phe Phe Ala Val Met Trp Tyr
                275                 280                 285
Tyr Ser Pro Lys Leu Thr Leu Val Ile Leu Phe Ser Leu Pro Cys Tyr
290                 295                 300
Ala Ala Trp Ser Val Phe Ile Ser Pro Ile Leu Arg Arg Arg Leu Asp
305                 310                 315                 320
Asp Lys Phe Ser Arg Asn Ala Asp Asn Gln Ser Phe Leu Val Glu Ser
                325                 330                 335
Val Thr Ala Ile Asn Thr Ile Lys Ala Met Ala Val Ser Pro Gln Met
                340                 345                 350
Thr Asn Ile Trp Asp Lys Gln Leu Ala Gly Tyr Val Ala Ala Gly Phe
                355                 360                 365
Lys Val Thr Val Leu Ala Thr Ile Gly Gln Gln Gly Ile Gln Leu Ile
                370                 375                 380
Gln Lys Thr Val Met Ile Ile Asn Leu Trp Leu Gly Ala His Leu Val
385                 390                 395                 400
Ile Ser Gly Asp Leu Ser Ile Gly Gln Leu Ile Ala Phe Asn Met Leu
                405                 410                 415
Ala Gly Gln Ile Val Ala Pro Val Ile Arg Leu Ala Gln Ile Trp Gln
                420                 425                 430
Asp Phe Gln Gln Val Gly Ile Ser Val Thr Arg Leu Gly Asp Val Leu
                435                 440                 445
Asn Ser Pro Thr Glu Ser Tyr His Gly Lys Leu Ala Leu Pro Glu Ile
450                 455                 460
```

Asn Gly Asp Ile Thr Phe Arg Asn Ile Arg Phe Arg Tyr Lys Pro Asp
465                 470                 475                 480

Ser Pro Val Ile Leu Asp Asn Ile Asn Leu Ser Ile Lys Gln Gly Glu
                485                 490                 495

Val Ile Gly Ile Val Gly Arg Ser Gly Ser Gly Lys Ser Thr Leu Thr
                500                 505                 510

Lys Leu Ile Gln Arg Phe Tyr Ile Pro Glu Asn Gly Gln Val Leu Ile
            515                 520                 525

Asp Gly His Asp Leu Ala Leu Ala Asp Pro Asn Trp Leu Arg Arg Gln
        530                 535                 540

Val Gly Val Val Leu Gln Asp Asn Val Leu Leu Asn Arg Ser Ile Ile
545                 550                 555                 560

Asp Asn Ile Ser Leu Ala Asn Pro Gly Met Ser Val Glu Lys Val Ile
                565                 570                 575

Tyr Ala Ala Lys Leu Ala Gly Ala His Asp Phe Ile Ser Glu Leu Arg
                580                 585                 590

Glu Gly Tyr Asn Thr Ile Val Gly Glu Gln Gly Ala Gly Leu Ser Gly
            595                 600                 605

Gly Gln Arg Gln Arg Ile Ala Ile Ala Arg Ala Leu Val Asn Asn Pro
        610                 615                 620

Lys Ile Leu Ile Phe Asp Glu Ala Thr Ser Ala Leu Asp Tyr Glu Ser
625                 630                 635                 640

Glu His Val Ile Met Arg Asn Met His Lys Ile Cys Lys Gly Arg Thr
                645                 650                 655

Val Ile Ile Ile Ala His Arg Leu Ser Thr Val Lys Asn Ala Asp Arg
                660                 665                 670

Ile Ile Val Met Glu Lys Gly Lys Ile Val Glu Gln Gly Lys His Lys
            675                 680                 685

Glu Leu Leu Ser Glu Pro Glu Ser Leu Tyr Ser Tyr Leu Tyr Gln Leu
        690                 695                 700

Gln Ser Asp
705

<210> SEQ ID NO 4
<211> LENGTH: 479
<212> TYPE: PRT
<213> ORGANISM: A. Aculeatus

<400> SEQUENCE: 4

His Met Lys Thr Trp Leu Met Gly Phe Ser Glu Phe Leu Leu Arg Tyr
1               5                   10                  15

Lys Leu Val Trp Ser Glu Thr Trp Lys Ile Arg Lys Gln Leu Asp Thr
                20                  25                  30

Pro Val Arg Glu Lys Asp Glu Asn Glu Phe Leu Pro Ala His Leu Glu
            35                  40                  45

Leu Ile Glu Thr Pro Val Ser Arg Arg Pro Arg Leu Val Ala Tyr Phe
        50                  55                  60

Ile Met Gly Phe Leu Val Ile Ala Phe Ile Leu Ser Val Leu Gly Gln
65                  70                  75                  80

Val Glu Ile Val Ala Thr Ala Asn Gly Lys Leu Thr Leu Ser Gly Arg
                85                  90                  95

Ser Lys Glu Ile Lys Pro Ile Glu Asn Ser Ile Val Lys Glu Ile Ile
            100                 105                 110

Val Lys Glu Gly Glu Ser Val Arg Lys Gly Asp Val Leu Leu Lys Leu
        115                 120                 125

-continued

```
Thr Ala Leu Gly Ala Glu Ala Asp Thr Leu Lys Thr Gln Ser Ser Leu
    130                 135                 140
Leu Gln Ala Arg Leu Glu Gln Ile Arg Tyr Gln Ile Leu Ser Arg Ser
145                 150                 155                 160
Ile Glu Leu Asn Lys Leu Pro Glu Leu Lys Leu Pro Asp Glu Pro Tyr
                165                 170                 175
Phe Gln Asn Val Ser Glu Glu Val Leu Arg Leu Thr Ser Leu Ile
                180                 185                 190
Lys Glu Gln Phe Ser Thr Trp Gln Asn Gln Lys Tyr Gln Lys Glu Leu
                195                 200                 205
Asn Leu Asp Lys Lys Arg Ala Glu Arg Leu Thr Ile Leu Ala Arg Ile
    210                 215                 220
Asn Arg Tyr Glu Asn Val Ser Arg Val Glu Lys Ser Arg Leu Asp Asp
225                 230                 235                 240
Phe Arg Ser Leu Leu His Lys Gln Ala Ile Ala Lys His Ala Val Leu
                245                 250                 255
Glu Gln Glu Asn Lys Tyr Val Gly Ala Ala Asn Glu Leu Arg Val Tyr
                260                 265                 270
Lys Ser Gln Leu Glu Gln Ile Glu Ser Glu Ile Leu Ser Ala Lys Glu
                275                 280                 285
Glu Tyr Gln Leu Val Thr Gln Leu Phe Lys Asn Glu Ile Leu Asp Lys
    290                 295                 300
Leu Arg Gln Thr Thr Asp Ser Ile Glu Leu Leu Thr Leu Glu Leu Glu
305                 310                 315                 320
Lys Asn Glu Glu Arg Gln Gln Ala Ser Val Ile Arg Ala Pro Val Ser
                325                 330                 335
Gly Lys Val Gln Gln Leu Lys Val His Thr Glu Gly Gly Val Val Thr
                340                 345                 350
Thr Ala Glu Thr Leu Met Val Ile Val Pro Glu Asp Asp Thr Leu Glu
    355                 360                 365
Val Thr Ala Leu Val Gln Asn Lys Asp Ile Gly Phe Ile Asn Val Gly
    370                 375                 380
Gln Asn Ala Ile Ile Lys Val Glu Ala Phe Pro Tyr Thr Arg Tyr Gly
385                 390                 395                 400
Tyr Leu Val Gly Lys Val Lys Asn Ile Asn Leu Asp Ala Ile Glu Asp
                405                 410                 415
Gln Lys Leu Gly Leu Val Phe Asn Val Ile Val Ser Val Glu Glu Asn
                420                 425                 430
Asp Leu Ser Thr Gly Asn Lys His Ile Pro Leu Ser Ser Gly Met Ala
    435                 440                 445
Val Thr Ala Glu Ile Lys Thr Gly Met Arg Ser Val Ile Ser Tyr Leu
    450                 455                 460
Leu Ser Pro Leu Glu Glu Ser Val Thr Glu Ser Leu His Glu Arg
465                 470                 475
```